(12) United States Patent  
Suganuma et al.

(10) Patent No.: US 10,716,875 B2  
(45) Date of Patent: Jul. 21, 2020

(54) INTRAOCULAR LENS

(71) Applicant: MENICON CO., LTD., Nagoya-shi, Aichi (JP)

(72) Inventors: Yuya Suganuma, Owariasahi (JP); Hiroko Nomura, Nagoya (JP); Tatsuya Ojio, Kasugai (JP); Keishi Tsukamoto, Kasugai (JP)

(73) Assignee: MENICON CO., LTD, Nagoya-shi (JP)

( * ) Notice: Subject to any disclaimer, the term of this patent is extended or adjusted under 35 U.S.C. 154(b) by 104 days.

(21) Appl. No.: 16/084,717

(22) PCT Filed: Jan. 31, 2018

(86) PCT No.: PCT/IB2018/000150  
§ 371 (c)(1),  
(2) Date: Sep. 13, 2018

(87) PCT Pub. No.: WO2019/150147  
PCT Pub. Date: Aug. 8, 2019

(65) Prior Publication Data  
US 2020/0038548 A1 Feb. 6, 2020

(51) Int. Cl.  
*A61L 27/16* (2006.01)  
*C08F 220/18* (2006.01)  
(Continued)

(52) U.S. Cl.  
CPC .......... *A61L 27/16* (2013.01); *C08F 220/18* (2013.01); *C08F 220/28* (2013.01);  
(Continued)

(58) Field of Classification Search  
CPC .... A61L 27/16; A61L 2430/16; C08F 220/18; C08F 220/1802; C08F 220/28; C08F 220/30  
See application file for complete search history.

(56) References Cited

U.S. PATENT DOCUMENTS 6,140,438 A * 10/2000 Ojio .................. A61L 27/16  
                                                        526/264  
2002/0027302 A1* 3/2002 Benz .................. A61F 2/1616  
                                                        264/1.38

FOREIGN PATENT DOCUMENTS

| JP | H11-56998 A | 3/1999 |
|---|---|---|
| JP | 2006-291006 A | 10/2006 |

(Continued)

OTHER PUBLICATIONS

Jun. 19, 2018 International Search Report issued in International Application No. PCT/IB2018/000150.

(Continued)

*Primary Examiner* — Vu A Nguyen  
(74) *Attorney, Agent, or Firm* — Oliff PLC

(57) ABSTRACT

An intraocular lens includes a polymeric lens material formed from a polymerizable composition. The polymerizable composition includes: (a) a single aromatic acrylate monomer which is an aromatic-ring containing acrylate; (b) an alkoxyalkyl methacrylate monomer having an alkoxyalkyl group with 4 or less carbon atoms; (c) an alkyl acrylate monomer having an alkyl group with 1 to 20 carbon atoms; (d) a hydrophilic monomer; and (e) a crosslinkable monomer.

14 Claims, 4 Drawing Sheets

(51) Int. Cl.
 *C08F 220/28* (2006.01)
 *C08F 220/30* (2006.01)
(52) U.S. Cl.
 CPC ........ *C08F 220/30* (2013.01); *C08F 220/281* (2020.02); *C08F 220/301* (2020.02); *C08F 2800/10* (2013.01); *C08F 2800/20* (2013.01); *C08F 2810/20* (2013.01); *C08F 2810/50* (2013.01)

(56) References Cited

FOREIGN PATENT DOCUMENTS

| WO | WO-2012004746 A2 * | 1/2012 | ............ C08F 220/30 |
| WO | WO-2013040434 A1 * | 3/2013 | ............... A61F 2/16 |

OTHER PUBLICATIONS

Jun. 19, 2018 Written Opinion of the International Searching Authority issued in International Application No. PCT/IB2018/000150.

* cited by examiner

INTRAOCULAR LENS

TECHNICAL FIELD

The disclosed embodiments relate to an intraocular lens that can be surgically implanted as a replacement for the natural crystalline lens in the eye. For example, the lens can be implanted into the capsule of the eye after surgical removal of the natural lens to treat cataracts.

BACKGROUND

Cataracts occur when the crystalline lens of the eye becomes cloudy. The cataracts may be in both eyes, and may cause fading vision and eventual blindness. Cataracts are the most common cause of vision loss in people over age 40, and the condition is the principal cause of blindness in the world.

Cataracts must be surgically removed to eliminate the cloudiness and restore vision. During cataract surgery, the cloudy natural lens is removed and replaced with a clear artificial lens called an intraocular lens, which is inserted into the lens capsule through a small incision.

As developments have been made in the field of small-incision cataract surgery, the size of the surgical incision has been decreased to promote shorter healing times, in particular, to enable out-patient surgeries. To deliver an intraocular lens through such a small incision, the lens material should be foldable and exhibit favorable shape recoverability. Accordingly, in addition to having optical properties necessary for a lens, soft materials that are flexible and foldable have been investigated for suitability in producing intraocular lenses.

Acrylic materials have a high refractive index and will slowly unfold after being implanted into the eye to recover the original lens shape, and thus are desirable candidates for polymeric lens materials. However, as the shape recoverability of the lens material is increased, the elongation percentage is generally reduced. A material with poor elongation percentage is fragile and easily tears, and thus cannot be reliably folded and unfolded for delivery via a small incision site without cracking or tearing. Accordingly, shape recoverability and elongation percentage are competing properties.

As an example of an acrylic lens material, a polymer can be obtained by polymerizing a hydrophilic monomer including a hydroxyl group-containing alkyl (meth) acrylate, a (meth) acrylamide monomer, and N-vinyl lactam to produce a polymer having a water absorption rate of 1.5 to 4.5% by mass (for example, refer to JP-A-11-56998). Although this material is flexible, ester linkages in the polymer structure undergo hydrolysis, and the hydrolyzate can then be eluted from the lens, potentially causing contamination and chemical irritation of the surrounding eye structure.

SUMMARY

It is desirable to develop a material for intraocular lenses that exhibits excellent flexibility without undergoing hydrolysis. The material also preferably exhibits excellent transparency, excellent shape recoverability, high refractive index, high breaking stress (elasticity), excellent flexibility, optimal tackiness, and minimal glistening. It is difficult to achieve all these properties simultaneously.

The disclosed embodiments include an intraocular lens comprising a polymeric lens material formed from a polymerizable composition. The polymerizable composition comprises: (a) a single aromatic acrylate monomer which is an aromatic-ring containing acrylate; (b) an alkoxyalkyl methacrylate monomer having an alkoxyalkyl group with 4 or less carbon atoms; (c) an alkyl acrylate monomer having an alkyl group with 1 to 20 carbon atoms; (d) a hydrophilic monomer; and (e) a crosslinkable monomer.

DETAILED DESCRIPTION OF EMBODIMENTS

The disclosed embodiments include an intraocular lens that is made from a unique polymer material. The lens has desirable physical, optical, and chemical properties that enable it to be surgically implanted as a replacement for the natural crystalline lens in the eye to restore vision after cataract surgery.

The polymeric lens material is made from a polymerizable composition comprising monomers. At warmer temperatures, such as body temperature or the temperature inside the typical operating room, the polymeric lens material becomes flexible and foldable, which assists in implanting the lens as described below. In this regard, the polymer lens material can have a glass transition temperature (Tg) that is at or below room temperature (~25° C.).

In order to provide optimal vision correction, the lens can exhibit excellent transparency and minimal glistening. "Glistening" is an imperfection in the lens that results from the formation of fluid-filled microvacuoles. These microvacuoles form as water accumulates inside the lens upon condensation and becomes trapped in the hydrophobic material, unable to disperse into the lens or otherwise exit the lens material. The wearer experiences glare and a "dazzling" effect as the microvacuoles refract light. The lens described herein can have an appropriate water absorption rate in order to control glistening.

The lens can also undergo minimal hydrolysis when exposed to an aqueous environment, and thus will not elute substantial hydrolyzates (chemical irritants) into the eye over time.

Intraocular Lens Structure

Figure 1:
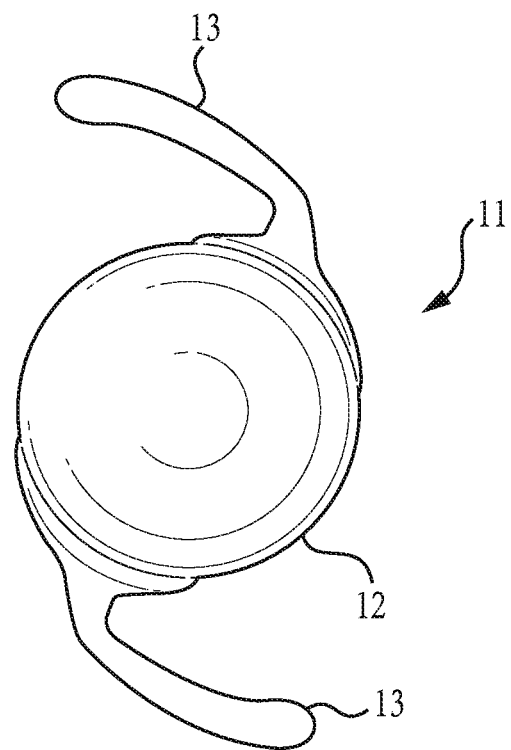
FIG. 1 is a plan view of an intraocular lens.

As shown in FIG. 1, the intraocular lens 11 includes a central optic 12, which is typically convex and mimics the focusing properties of the natural lens, and a pair of haptics 13, which extend from the optic and function as optic positioning elements. The optic 12 and haptics 13 can be made of the same or different material. The haptics 13 can be bonded to the optic 12 to form a 3-piece lens, or can be integrally formed with the optic 12 to provide a 1-piece (monolithic) lens (as shown in FIG. 1).

Lens Manufacturing Method

The polymeric lens material of the disclosed embodiments can be shaped into an intraocular lens using shaping methods that are commonly employed by those skilled in the art. For example, the lens can be shaped using a cutting and grinding method or a molding method. In the cutting and grinding method, the polymerizable composition is polymerized in a mold or vessel designed to facilitate shaping of an intraocular lens, to obtain a rod-, block-, or plate-shaped polymeric starting material. The starting material is then processed into the desired shape by mechanical processing such as cutting, grinding, or polishing. In the molding method, a mold corresponding to the shape of the desired intraocular lens is first prepared, and then the polymerizable composition is polymerized in this mold to obtain a polymeric molded product, which may further be subjected to mechanical finishing treatment, if necessary. The above-mentioned mold or vessel may be made of glass or a plastic such as polyethylene or polypropylene.

Surgical Implantation

Figure 2:
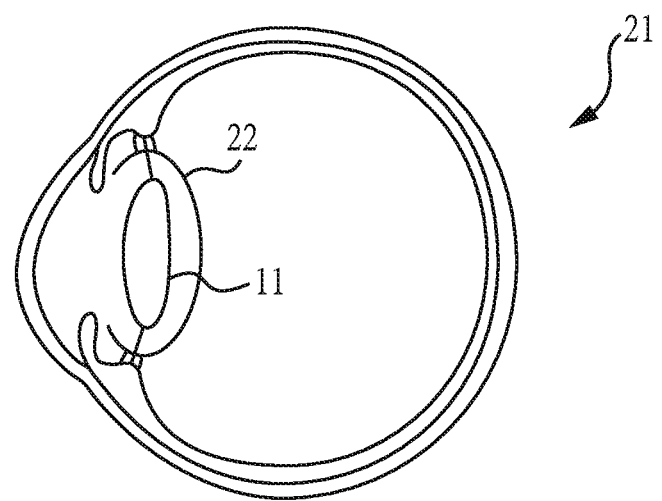
FIG. 2 is a side cross-sectional view of an eye in which an intraocular lens has been implanted.

During cataract surgery, a small incision is made, the cloudy portions of the natural lens are removed by phacoemulsification, and the intraocular lens 11 is inserted through the incision and positioned within the lens capsule 22 (FIG. 2). The surgical incision should be as small as possible to promote shorter healing times. If the incision is small enough, the eye will undergo self-healing without any need for sutures or other intervention. In this case, the surgery can be performed as an out-patient procedure and the patient can quickly return to their daily tasks. The positioning of the lens 11 within the lens capsule 22 of the eye 21 is depicted in FIG. 2. The haptics 13 slowly expand once positioned to hold the lens 11 in place by pressing against the inside of the lens capsule 22 by spring force.

Figure 3:
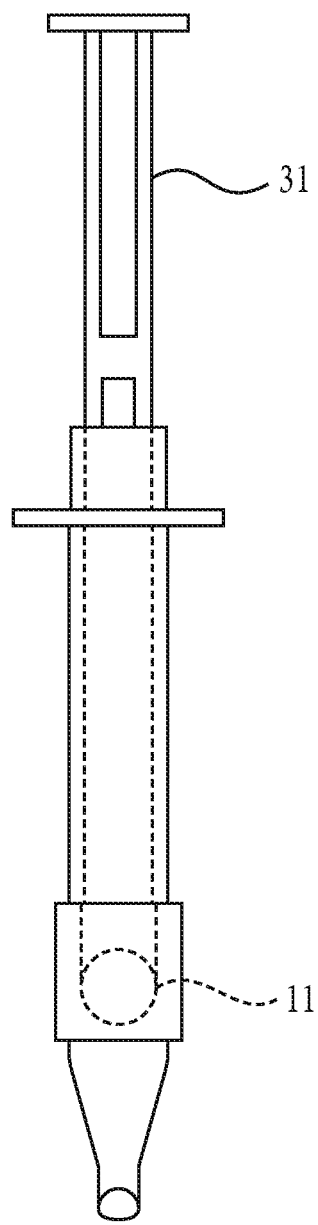
FIG. 3 shows an injector device for implanting the intraocular lens.

In order for the lens to be delivered through such a small incision, the lens 11 is implanted using the injector device 31 shown in FIG. 3. The lens 11 is loaded into the injector device 31 together with a viscoelastic fluid (not shown). As the lens 11 is pushed out of the injector device 31 together with the fluid, the lens 11 folds and assumes a narrow profile that allows it to fit through a very small incision. The haptics cross over the optic, and the optic folds in half, sandwiching the haptics within the optic. The lens 11 begins to unfold once it completely exits the injector device 31.

In order to be appropriately positioned within the lens capsule, the lens should have some degree of tackiness. However, if the lens has excessive tackiness it will not adequately unfold during the implantation step because the lens material will stick to itself.

Likewise, in order to withstand delivery, the lens of the disclosed embodiments can exhibit other material properties that complement folding and unfolding of the material. In particular, the lens can have high breaking stress, high elongation characteristic, and good balance of flexibility and strength. Because of the high breaking stress and elongation characteristic, the lens can withstand large stresses and tensile deformation without failing (e.g., tears or punctures).

The lens should also have adequate optical properties, including a high refractive index, which enables a high focal strength to be achieved even with a comparatively smaller lens size.

Polymeric Lens Material

The intraocular lens includes a polymeric lens material that can achieve the unique combination of properties described above. The lens material includes an aromatic ring-containing acrylate structure, an alkoxyalkyl methacrylate structure having an alkoxyalkyl group having 4 or less carbon atoms, a hydrophilic structure based on a hydrophilic monomer, and a crosslinked structure based on a crosslinkable monomer. The lens material may also include an alkyl acrylate structure in which the alkyl group has 1 to 20 carbon atoms.

The lens material as described above is formed from a polymerizable composition comprising an aromatic acrylate monomer (an aromatic-ring containing acrylate), an alkoxyalkyl methacrylate monomer having an alkoxyalkyl group with 4 or less carbon atoms, a hydrophilic monomer, and a crosslinkable monomer. The polymerizable composition may also include an alkyl acrylate monomer having an alkyl group with 1 to 20 carbon atoms.

The "base material" of this polymerizable composition as used herein includes the aromatic acrylate monomer, the alkoxyalkyl methacrylate monomer, and, if present, the alkyl acrylate monomer. Similarly, the structures formed by polymerizing these monomers collectively form the base material of the polymeric lens material.

For example, as shown in the below Chemical Formula (1), the lens material may contain an aromatic ring-containing acrylate structure A, an alkoxyalkyl methacrylate structure B, and an alkyl acrylate structure C. Collectively, these structures are considered the base material of the lens polymer.

Chemical Formula (1)

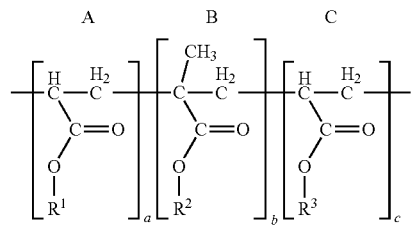

In the Chemical Formula (1), a, b and c are arbitrary integers, and the aromatic ring-containing acrylate structure A, the alkoxyalkyl methacrylate structure B, and the alkyl acrylate structure C can be bonded in random sequence within the carbon chain. Thus, adjacent structures may be different or may be the same. The functional group $R^1$ is a functional group containing an aromatic ring; the functional group $R^2$ is an alkoxyalkyl group containing an alkoxy group having 4 or less carbon atoms; and the functional group $R^3$ is an alkyl group having 1 to 20 carbon atoms. Hereinafter, the acrylate having an acryloyl group and the methacrylate having a methacryloyl group are each referred to as "(meth) acrylate." For convenience of explanation, the constituent moieties contained in the polymer are specified by the name of the monomer, and the monomers exemplified in the explanation of the structure of the polymer are those having a structure in which the polymerizable group is bonded to other constituent moieties. For example, in the explanation of the structure of a polymer, what is exemplified as "(meth) acrylate" exists as a "(meth) acrylate structure" in the polymer, which means that the double bonds of the (meth) acrylate groups are bonded (polymerized) to the polymer backbone.

In the lens material, the aromatic ring-containing acrylate structure is a structure based on an aromatic ring-containing acrylate as a base monomer. The aromatic ring-containing acrylate affects the refractive index of the lens material. The aromatic ring-containing acrylate structure may have a phenoxy group, an alkylene group having 2 or less carbon atoms, and an acrylate bonding site. The polymerizable composition can include a single aromatic-ring containing acrylate, where "single" means that the polymer has only one aromatic-ring containing acrylate, optionally including at most negligible amounts of other aromatic-ring containing acrylates (i.e., less than 3.0 parts per 100 parts of the base material).

Examples of the aromatic ring-containing acrylate include phenoxyethyl acrylate, phenylethyl acrylate, benzyl acrylate, phenyl acrylate, pentabromophenyl acrylate, and the like. Among them, one or more of phenoxyethyl acrylate, phenylethyl acrylate, and benzyl acrylate is preferable from the viewpoint of increasing the refractive index, and phenoxyethyl acrylate is particularly preferable from the viewpoint of also improving flexibility. Even more preferably, phenoxyethyl acrylate is the only aromatic-ring containing acrylate in the entire polymerizable composition (i.e., the polymerizable composition and lens material do not contain any other aromatic-ring containing acrylates).

Since it is desirable that the lens exhibits a high refractive index even in the water absorbing (hydrated) state, the content of the aromatic acrylate can be 30 parts by mass or more and 80 parts by mass or less, 40 parts by mass or more and 70 parts by mass or less, or 55 parts by mass or more and 65 parts by mass or less per 100 parts by 0 mass of the base material. For example, the content of the aromatic acrylate may be 55, 56, 57, 58, 59, 60, 61, 62, 63, 64, or 65 parts by mass with respect to 100 parts by mass of the base material.

The molar amount of the aromatic ring-containing acrylate in the polymerizable composition can be 19 mol % to 46 mol %, 34 mol % to 43 mol %, or 35 mol % to 39 mol %.

The methacrylate structure in the lens polymer (from the alkoxyalkyl methacrylate) has a relatively hard (rigid) structure due to the presence of a methyl group as compared with acrylate. However, the structure is less susceptible to water attack and is therefore resistant to hydrolysis.

The number of carbons in the alkoxyalkyl group (4 or less carbon atoms) also affects the degree of glistening, tackiness, and flexibility. The number of carbon groups in the alkoxyalkyl group is controlled so that the methacrylate structure is not too hard, and thus provides sufficient flexibility.

The alkoxyalkyl group may be represented by, for example, the following Chemical Formula (2):

$$C_n H_{2n+1} O C_m H_{2m} \quad \text{Chemical Formula (2)}$$

In the Chemical Formula (2), (n+m)≤4.

The alkoxyalkyl methacrylate structure having an alkoxyalkyl group having 4 or less carbon atoms has a structure based on alkoxyalkyl methacrylate as a base monomer. The alkoxyalkyl group of the alkoxyalkyl methacrylate may be represented by, for example, the above Chemical Formula (2). Examples of the alkoxy group include a methoxy group, an ethoxy group, and the like. Examples of the alkylene group to which the alkoxy group is bonded include a methylene group, an ethylene group, and the like. The alkoxyalkyl methacrylate is preferably one or more of methoxyethyl methacrylate and ethoxyethyl methacrylate, more preferably ethoxyethyl methacrylate.

The content of the alkoxyalkyl methacrylate in the polymerizable composition can be in the range of 5 parts by mass or more and 70 parts by mass or less, 6 parts by mass or more and 30 parts by mass or less, or 10 parts by mass or more and 25 parts by mass or less per 100 parts by mass of the base material, from the viewpoint of inhibiting hydrolysis and facilitating folding. For example, the content of the alkoxyalkyl methacrylate may be 10, 11, 12, 13, 14, 15, 16, 17, 18, 19, 20, 21, 22, 23, 24, or 25 parts by mass with respect to 100 parts by mass of the base material.

The molar amount of the alkoxyalkyl methacrylate in the polymerizable composition can be 5 mol % to 55 mol %, 6 mol % to 30 mol %, or 7 mol % to 20 mol %.

The alkyl acrylate structure in which the alkyl group has 1 to 20 carbon atoms is a structure based on alkyl acrylate as a base monomer. The alkyl acrylate having 1 to 20 carbon atoms in the alkyl group can affect shape recoverability and flexibility of the polymeric lens material. Examples of the alkyl acrylate include straight-chain, branched-chain or cyclic alkyl acrylate and the like, such as methyl acrylate, ethyl acrylate, propyl acrylate, butyl acrylate, pentyl acrylate, hexyl acrylate, heptyl acrylate, nonyl acrylate, stearyl acrylate, octyl acrylate, decyl acrylate, lauryl acrylate, pentadecyl acrylate, 2-ethylhexyl acrylate, cyclopentyl acrylate, and cyclohexyl acrylate. These may be used alone or in combination. Among them, from the viewpoint of improving shape recoverability and flexibility, an alkyl acrylate having an alkyl group having 1 to 5 carbon atoms is preferable, and ethyl acrylate or butyl acrylate is particularly preferable. In view of improving copolymerizability, ethyl acrylate is most preferable.

The content of the alkyl acrylate in the polymerizable composition is in the range of 0 parts by mass or more and 35 parts by mass or less per 100 parts by mass of the base material. The content of the alkyl acrylate can be in the range of 5 parts by mass or more and 34 parts by mass or less, or 10 parts by mass or more and 30 parts by mass or less per 100 parts by mass of the base material, from the viewpoint of improving flexibility and shape recoverability. For example, the content of the alkyl acrylate may be 15, 16, 17, 18, 19, 20, 21, 22, 23, 24, 25, 26, 27, 28, 29, or 30 parts by mass per 100 parts by mass of the base material.

The molar amount of the alkyl acrylate in the polymerizable composition can be 0 mol % to 45 mol %, 10 mol % to 40 mol %, or 20 mol % to 37 mol %.

In one embodiment, the base material of the polymeric lens material may consist of the structures formed from polymerizing 2-phenoxyethyl acrylate (POEA), ethyl acrylate (EA), and ethoxyethyl methacrylate (ETMA), as shown in the following Chemical Formula (3).

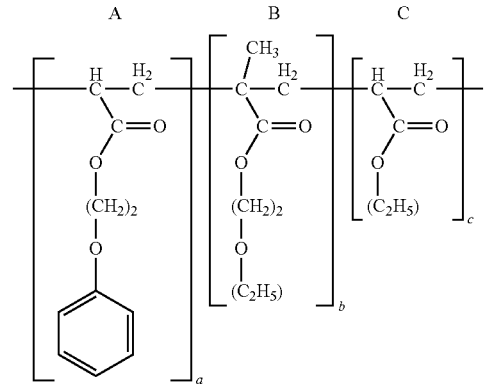

Chemical Formula (3)

In the Chemical Formula (3), a, b and c are arbitrary integers, and the aromatic ring-containing acrylate structure A, the alkoxyalkyl methacrylate structure B, and the alkyl acrylate structure C can be randomly bonded to the carbon chain (adjacent structures may be different or may be the same).

In the polymeric lens material, the hydrophilic structure is a structure based on a hydrophilic monomer. This hydrophilic monomer is a component that imparts hydrophilicity to the lens material, and reduces the likelihood of glistening in the material. The hydrophilic monomer may include, for example, one or more of a hydroxyl group-containing alkyl (meth) acrylate having an alkyl group of 1 to 20 carbon atoms, a (meth) acrylamide monomer, and an N-vinyl lactam. Further, it may contain other hydrophilic monomers. Examples of the hydroxyl group-containing alkyl (meth) acrylate include a hydroxyalkyl (meth) acrylate such as hydroxyethyl (meth) acrylate, hydroxypropyl (meth) acrylate, hydroxybutyl (meth) acrylate, hydroxypentyl (meth) acrylate, dihydroxypropyl (meth) acrylate, dihydroxybutyl (meth) acrylate, dihydroxy pentyl (meth) acrylate, and the like. Examples of the (meth) acrylamide monomer include N,N-dialkyl (meth) acrylamides such as N,N-dimethyl (meth) acrylamide, N,N-diethyl (meth) acrylamide, N,N-dipropyl (meth) acrylamide, and the like, or N,N-dialkylaminoalkyl (meth) acrylamides such as N,N-dimethylaminopropyl (meth) acrylamide, N,N-diethylaminopropyl (meth) acrylamide, and the like. Examples of the N-vinyl lactam include N-vinyl pyrrolidone, N-vinyl piperidone, N-vinyl caprolactam, and the like. Examples of other hydrophilic monomers include diethylene glycol mono (meth) acrylate, triethylene glycol mono (meth) acrylate, propylene glycol mono (meth) acrylate, (meth) acrylic acid, 1-methyl-3-metylene-2-pyrrolidinone, maleic anhydride, maleic acid, maleic acid derivatives, fumaric acid, fumaric acid derivatives, aminostyrene, hydroxystyrene, and the like. The above-mentioned hydrophilic monomers can be used alone or in combination. Among these hydrophilic monomers, hydroxyl group-containing alkyl (meth) acrylate and (meth) acrylamide monomers are preferable, and 2-hydroxyethyl methacrylate is particularly preferable, from the viewpoint of reducing glistening.

The content of the hydrophilic monomer in the polymerizable composition can be in the range of 10 parts by mass or more and 45 parts by mass or less per 100 parts by mass of the base material. Within this range, it is possible to sufficiently manifest the effect of promoting the reduction of glistening, without hampering the ability to fold the lens when in the dry state (in preparation for implantation). Additionally, the content of the hydrophilic monomer can be in the range of 15 parts by mass or more and 30 parts by mass or less with respect to 100 parts by mass of the base material. For example, the content of the hydrophilic monomer may be 15, 16, 17, 18, 19, 20, 21, 22, 23, 24, 25, 26, 27, 28, 29, or 30 parts by mass with respect to 100 parts by mass of the base material.

Additionally, the molar amount H of the hydrophilic monomer in the polymerizable composition can be 10 mol % to 40 mol %, 13 mol % to 25 mol %, or 15 mol % to 24 mol %. When the molar amount H of the hydrophilic monomer falls within these ranges, glistening can be reduced while also achieving desirable flexibility.

The crosslinking structure is a structure based on a crosslinkable monomer. This crosslinkable monomer may affect the flexibility of the polymeric lens material, imparting good mechanical strength, further improving shape recoverability, and improving the copolymerizability of the polymerization components such as hydrophilic monomers and other polymerizable monomers. Examples of the crosslinkable monomer include butanediol di (meth) acrylate, ethylene glycol di (meth) acrylate, diethylene glycol di (meth) acrylate, triethylene glycol di (meth) acrylate, propylene glycol di (meth) acrylate, dipropylene glycol di (meth) acrylate, diallyl fumarate, allyl (meth) acrylate, vinyl (meth) acrylate, trimethylolpropane tri (meth) acrylate, methacryloyloxyethyl (meth) acrylate, divinylbenzene, diallyl phthalate, diallyl adipate, triallyl diisocyanate, α-methylene-N-vinylpyrrolidone, 4-vinylbenzyl (meth) acrylate, 3-vinylbenzyl (meth) acrylate, 2,2-bis ((meth) acryloyloxyphenyl) hexafluoropropane, 2,2-bis ((meth) acryloyloxyphenyl) propane, 1,4-bis (2-(meth) acryloyloxyhexafluoroisopropyl) benzene, 1,3-bis (2-(meth) acryloyloxyhexafluoroisopropyl) benzene, 1,2-bis (2-(meth) acryloyloxyhexafluoroisopropyl) benzene, 1,4-bis (2-(meth) acryloyloxyisopropyl) benzene, 1,3-bis (2-(meth) acryloyloxyisopropyl) benzene, 1,2-bis (2-(meth) acryloyloxyisopropyl) benzene, and the like. These may be used alone or in combination of two or more. Among these crosslinkable monomers, one or more of butanediol di (meth) acrylate and ethylene glycol di (meth) acrylate are preferred, and butanediol diacrylate is particularly preferred from the viewpoint of controlling flexibility, conferring good mechanical strength, and improving shape recoverability and copolymerizability.

The crosslinkable monomer in the polymerizable composition can be present in a range of 1 parts by mass or more and 6 parts by mass or less, or 2 parts by mass or more and 4 parts by mass or less, per 100 parts by mass of the base material. When the content is 2 parts by mass or more, shape recoverability can be improved and glistening is suppressed. When the content is 4 parts by mass or less, the lens material has an elongation percentage reflective of being able to withstand insertion through a small incision without cracking or tearing. For example, the content of the crosslinkable monomer may be 2, 3, or 4 parts by mass with respect to 100 parts by mass of the base material.

Additionally, the molar amount C of the crosslinkable monomer in polymerizable composition can be 0.9 mol % to 3.1 mol %, 1.0 mol % to 2.6 mol %, or 1.1 mol % to 2.1 mol %.

An H×C value of the polymerizable composition can be more than $1.7 \times 10^{-3}$ and less than $8.1 \times 10^{-3}$, more than $1.8 \times 10^{-3}$ and less than $5.5 \times 10^{-3}$, or more than $2.4 \times 10^{-3}$ and less than $4.5 \times 10^{-3}$, the H×C value being the product of the molar amount H of the hydrophilic monomer and the molar amount C of the crosslinkable monomer. Additionally, the H×C value can be $3.6 \times 10^{-3}$ or more and less than $4.2 \times 10^{-3}$. When the molar amounts of the hydrophilic monomer and crosslinkable monomer satisfy the disclosed ranges, hydrolysis can be even more effectively inhibited.

The molar ratio H:C (molar amount H of the hydrophilic monomer:molar amount C of the crosslinkable monomer) in the polymerizable composition can be from 5:1 to 20:1, from 8:1 to 16:1, or from 12:1 to 15:1.

Figure 4:
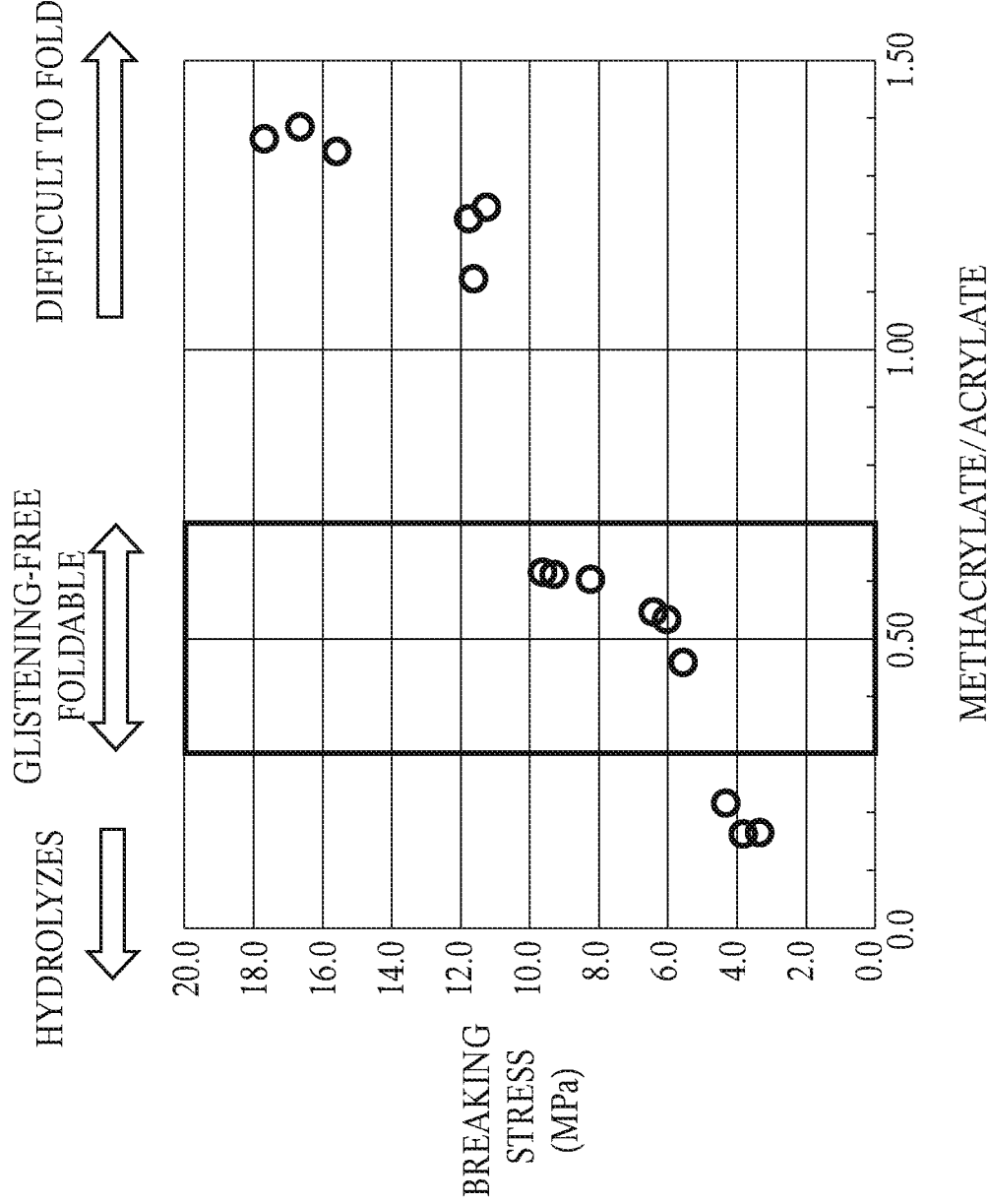
FIG. 4 is graph illustrating the relationship between breaking stress and both flexibility and susceptibility to hydrolysis as a function of the molar ratio of methacrylate components to acrylate components in the polymerizable composition used to form the polymeric lens material of the intraocular lens.

The ratio MA/A is the molar ratio of methacrylate components to acrylate components in the polymerizable composition. The ratio MA/A of the lens material can be in the range of 0.25 to 1.25, 0.30 to 0.70, 0.35 to 0.65, or 0.40 to 0.62. As shown in FIG. 4, it has been discovered that when the ratio MA/A is less than 0.3, the lens material can be susceptible to unwanted hydrolysis and glistening. When the ratio MA/A is greater than 0.7, the lens material can be difficult to fold. Accordingly, the lens material of the disclosed embodiments is readily foldable without being susceptible to glistening.

In addition to the base material, the hydrophilic structure, and the crosslinking structure, the lens material may contain other additives such as an ultraviolet absorber, an initiator, and a coloring matter (e.g., a dye).

Examples of the ultraviolet absorber include benzophenones such as 2-hydroxy-4-methoxybenzophenone and 2-hydroxy-4-octoxybenzophenone; benzotriazoles such as 2-(2'-hydroxy-5'-methacryloxyethyleneoxy-t-butylphenyl)-5-methyl-benzotriazole, 2-(2'-hydroxy-5'-methylphenyl) benzotriazole, 5-chloro-2 (3'-t-butyl-2'-hydroxy-5'-methyphenyl) benzotriazole; salicylic acid derivatives; hydroxyacetophenone derivatives; and the like. The blending amount of the ultraviolet absorber can be in the range of 0.05 parts by mass or more and 3 parts by mass or less with respect to 100 parts by mass of the base material, for example. For example, when correcting for cyanopia, it is desirable that the coloring matter is a yellow to orange coloring matter.

Examples of the coloring matter include dyes described in JP-A-2006-291006; oil-soluble dyes such as CI Solvent Yellow and CI Solvent Orange described in color index (CI); Disperse dyes such as CI Disperse Yellow and CI Disperse Orange; and vat type dyes. The blending amount of the coloring matter can be in the range of 0.001 part by mass or more and 3 parts by mass or less with respect to 100 parts by mass of the base material.

The polymerizable composition may be polymerized by adding, for example, a radical polymerization initiator or a photopolymerization initiator. The polymerization method may be, for example, a method in which a radical polymerization initiator is blended and then heated or irradiated with electromagnetic waves such as microwaves, ultraviolet rays, or radiation (γ rays). Examples of the radical polymerization initiator include azobisisobutyronitrile, azobisdimethylvaleronitrile, benzoyl peroxide, t-butyl hydroperoxide, cumene hydroperoxide, and the like.

When polymerization is carried out using light or the like, a photopolymerization initiator and a sensitizer can be added. Examples of the photopolymerization initiator include benzoin compounds such as methyl orthobenzoyl benzoate, phenone compounds such as 2-hydroxy-2-methyl-1-phenylpropane-1-one, thioxanthone compounds such as 1-hydroxycyclohexyl phenyl ketone, 1-phenyl-1,2-propanedione-2-(o-ethoxycarbonyl) oxime, and 2-chlorothioxanthone, dibenzosuberone, 2-ethylanthraquinone, benzophenone acrylate, benzophenone, benzyl, and the like. In order to allow the polymerization reaction to proceed at a sufficient rate, the amount of the polymerization initiator and the sensitizer to be used should be in the range of 0.01 parts by mass or more and 2 parts by mass or less with respect to 100 parts by mass of the base material.

Physical Properties

The polymeric lens material of some embodiments described herein is not susceptible to significant glistening. As evaluated according to the experimental method described herein, the number of occurrences of glistening is preferably 15 or less per lens. When the material is formed into a plate, the number of occurrences of glistening when evaluated by the same method is preferably 6 or less per plate, more preferably 2 or less.

Additionally, little to no hydrolyzate elutes from embodiments of the lens material in aqueous solution. The degree of hydrolyzate elution can be assessed by measuring the elution rate of a hydrolyzate of the aromatic ring-containing acrylate (for example, the elution rate of phenoxyethyl alcohol (POEtOH), which is a hydrolyzate of 2-phenoxyethyl acrylate (POEA)), when the lens material is stored in water at 100° C. for 30 days, 60 days, and 90 days. The elution rate at 30 days is preferably 0.15 mass % or less, 0.14 mass % or less, 0.13 mass % or less, or 0.10 mass % or less. The elution rate of POEtOH from the lens material when stored at 100° C. for 60 days in water is preferably 0.80 mass %, 0.75 mass % or less, 0.70 mass % or less, or 0.50 mass % or less. The elution rate of POEtOH from the material when stored at 100° C. for 90 days in water is preferably 3.30 mass % or less, and more preferably 2.80 mass % or less, 2.40 mass % or less, or 1.30 mass % or less. Herein, the term "elution characteristic" means the elution rate of a hydrolyzate of the aromatic ring-containing acrylate within a particular time frame under the conditions described above. For example, an "elution characteristic of 0.13 mass % or less at 30 days" means that the material exhibits a hydrolyzate elution rate of 0.13 mass % or less when the material is stored in water at 100° C. for 30 days.

Embodiments of the lens material have a refractive index of 1.50 or more in a state of hydration (a moistened state).

Embodiments of the polymeric lens material have a suitable breaking stress. For example, the lens material can have a breaking stress of from 4.5 MPa to 12.0 MPa, and more preferably from 5.5 MPa to 11.0 MPa or from 8.0 MPa to 10.0 MPa. The material having the described breaking stress exhibits favorable elasticity, and can be folded and delivered through a small incision without breaking.

The polymeric lens material has an elongation characteristic that allows for insertion through a small incision without cracking or tearing. Specifically, when the material is evaluated according to the experimental method described herein, the elongation characteristic is preferably 170% or more. In addition, from the viewpoint of shape recoverability of the polymeric lens material, the elongation characteristic is preferably 600% or less. Herein, the term "elongation characteristic" means the elongation percentage of a dumbbell shaped test piece formed from the lens material tested under the conditions described below (see "Elongation percentage" below). For example, a lens material having an "elongation characteristic of 170%" would exhibit an elongation percentage of 170% if formed into a dumbbell shaped test piece having a total length of about 20 mm, a parallel part length of 6 mm, a parallel part width of 1.5 mm, and a thickness of 0.8 mm and pulled at a speed of 100 mm/min until breaking after having been immersed in constant-temperature water at 25° C. and allowed to stand for 1 minute.

The polymeric lens material preferably has a water absorption ratio of 1.5 mass % or more and 4.5 mass % or less. When the water absorption rate is 1.5 mass % or more, the occurrence of glistening can be suppressed, and when the water absorption ratio is 4.5 mass % or less, it is possible to further suppress deterioration of flexibility and deterioration of shape recoverability. The water absorption ratio of the lens material may be 2.0 mass % or more and 4.0 mass % or less, or 2.5 mass % or more and 3.5 mass % or less.

EXAMPLES

The abbreviations of the compounds used in the Experimental Examples are shown below.

<Base Material>

POEA: 2-phenoxyethyl acrylate
EA: ethyl acrylate
POEMA: phenoxyethyl methacrylate
EMA: ethyl methacrylate
BMA: butyl methacrylate
EHMA: ethyl hexyl methacrylate
LMA: lauryl methacrylate
MTMA: methoxyethyl methacrylate ETMA: ethoxyethyl methacrylate
<Hydrophilic Monomer>
HEMA: 2-hydroxyethyl methacrylate
<Crosslinkable Monomer>
BDDA: 1,4-butanediol diacrylate
[Preparation of Polymeric Material with Plate Shape or Lens Shape]

Experimental Examples 1 to 14

For each of Examples 1 to 14, the polymerizable composition shown in Table 1 and 0.5 parts by mass of 2,2′-azobis (2,4-dimethylvaleronitrile) as a polymerization initiator with respect to 100 parts by mass of the base material were mixed and injected into the lens-shaped mold. This mold was placed in an oven at 80° C. and subjected to heat polymerization molding for 40 minutes. The obtained polymer was released from the mold, subjected to elution treatment, and then dried in an oven at 60° C. to obtain lens-shaped polymeric materials.

Experimental Examples 15 to 60

Similarly, using the polymerizable compositions shown in Table 2, the mixture was injected into a mold having a desired plate shape and the same process as described above was carried out to obtain plate-shaped polymeric materials ("plates").

According to the measurements being performed, plates of two different thicknesses were prepared from each composition of Experimental Examples 15 to 60. The plate having a thickness of 0.5 mm or 0.8 mm described below is a plate made from a mold using a spacer having a thickness of 0.5 mm or 0.8 mm. In accordance with the purpose of the test, the dried plate was hollowed out to a diameter of 6 mm or 8 mm to prepare for measurement.

The compositions are identified in the Examples below on a mol % basis.

TABLE 1

| Sample | Base material | | | | | | Hydrophilic monomer | Crosslinkable monomer | | Acrylate | Methacrylate | |
|---|---|---|---|---|---|---|---|---|---|---|---|---|
| | POEA Mol % | EA Mol % | POEMA Mol % | EHMA Mol % | LMA Mol % | ETMA Mol % | (H) HEMA Mol % | (C) BDDA Mol % | (H × C) × 10⁻³ | Monomer (A) Mol % | Monomer (MA) Mol % | MA/A |
| Example 1 | 29.7 | 28.5 | | | 22.5 | | 16.4 | 2.9 | 4.7 | 61.1 | 38.9 | 0.64 |
| Example 2 | 51.6 | | | | 26.0 | | 19.0 | 3.3 | 6.4 | 54.9 | 45.1 | 0.82 |
| Example 3 | 43.0 | 27.5 | | | 10.8 | | 15.9 | 2.8 | 4.4 | 73.3 | 26.7 | 0.36 |
| Example 4 | 41.7 | 26.7 | | 13.5 | | | 15.4 | 2.7 | 4.2 | 71.1 | 28.9 | 0.41 |
| Example 5 | 18.7 | 47.8 | 17.4 | | | | 13.8 | 2.4 | 3.3 | 68.8 | 31.2 | 0.45 |
| Example 6 | | 71.7 | 14.9 | | | | 11.8 | 1.6 | 1.8 | 73.2 | 26.8 | 0.37 |
| Example 7 | 45.2 | | | | | 36.6 | 16.7 | 1.5 | 2.4 | 46.7 | 53.3 | 1.14 |
| Example 8 | 40.9 | 26.2 | | | | 16.6 | 15.1 | 1.3 | 2.0 | 68.4 | 31.6 | 0.46 |
| Example 9 | 40.7 | 26.1 | | | | 16.5 | 15.0 | 1.6 | 2.5 | 68.5 | 31.5 | 0.46 |
| Example 10 | 40.6 | 26.0 | | | | 16.4 | 15.0 | 2.0 | 3.0 | 68.6 | 31.4 | 0.46 |
| Example 11 | 41.7 | 20.0 | | | | 21.1 | 15.4 | 1.7 | 2.6 | 63.5 | 36.5 | 0.58 |
| Example 12 | 41.6 | 20.0 | | | | 21.1 | 15.4 | 2.0 | 3.1 | 63.6 | 36.4 | 0.57 |
| Example 13 | 42.8 | 13.7 | | | | 26.0 | 15.8 | 1.7 | 2.7 | 58.2 | 41.8 | 0.72 |
| Example 14 | 42.6 | 13.6 | | | | 25.9 | 15.7 | 2.1 | 3.3 | 58.4 | 41.6 | 0.71 |

TABLE 2

| Sample | Base material | | | | | | | Hydrophilic monomer | Crosslinkable monomer | | Acrylate | Methacrylate | |
|---|---|---|---|---|---|---|---|---|---|---|---|---|---|
| | POEA Mol % | EA Mol % | EMA Mol % | BMA Mol % | LMA Mol % | MTMA Mol % | ETMA Mol % | (H) HEMA Mol % | (C) BDDA Mol % | (H × C) × 10⁻³ | Monomer (A) Mol % | Monomer (MA) Mol % | MA/A |
| Example 15 | 39.1 | | 43.9 | | | | | 14.4 | 2.5 | 3.7 | 41.6 | 58.4 | 1.40 |
| Example 16 | 42.8 | | | 38.6 | | | | 15.8 | 2.8 | 4.4 | 45.6 | 54.4 | 1.19 |
| Example 17 | 43.0 | 27.5 | | | 10.8 | | | 15.9 | 2.8 | 4.4 | 73.3 | 26.7 | 0.36 |
| Example 18 | 43.1 | | | | | 38.3 | | 15.9 | 2.8 | 4.4 | 45.8 | 54.2 | 1.18 |
| Example 19 | 36.8 | 47.2 | | | | | | 13.6 | 2.4 | 3.2 | 86.4 | 13.6 | 0.16 |
| Example 20 | 40.3 | 25.8 | | | | | 16.3 | 14.9 | 2.6 | 3.9 | 68.8 | 31.2 | 0.45 |
| Example 21 | 44.6 | | | | | | 36.1 | 16.5 | 2.9 | 4.7 | 47.4 | 52.6 | 1.11 |

TABLE 3

| Sample | Base material POEA Mol % | Base material EA Mol % | Base material ETMA Mol % | Hydrophilic monomer (H) HEMA Mol % | Crosslinkable monomer (C) BDDA Mol % | (H × C) × 10⁻³ | Acrylate Monomer (A) Mol % | Methacrylate Monomer (MA) Mol % | MA/A |
|---|---|---|---|---|---|---|---|---|---|
| Example 22 | 37.1 | 47.4 |  | 13.7 | 1.8 | 2.5 | 86.3 | 13.7 | 0.16 |
| Example 23 | 40.6 | 26.0 | 16.4 | 15.0 | 2.0 | 3.0 | 68.6 | 31.4 | 0.46 |
| Example 24 | 44.9 |  | 36.4 | 16.6 | 2.2 | 3.6 | 47.1 | 52.9 | 1.12 |
| Example 25 | 37.3 | 47.7 |  | 13.8 | 1.2 | 1.7 | 86.2 | 13.8 | 0.16 |
| Example 26 | 39.0 | 37.4 | 7.9 | 14.4 | 1.3 | 1.8 | 77.7 | 22.3 | 0.29 |
| Example 27 | 40.9 | 26.2 | 16.6 | 15.1 | 1.3 | 2.0 | 68.4 | 31.6 | 0.46 |
| Example 28 | 41.9 | 20.1 | 21.2 | 15.5 | 1.4 | 2.1 | 63.3 | 36.7 | 0.58 |
| Example 29 | 45.2 |  | 36.6 | 16.7 | 1.5 | 2.4 | 46.7 | 53.3 | 1.14 |
| Example 30 | 35.3 | 45.1 |  | 17.4 | 2.3 | 4.0 | 82.6 | 17.4 | 0.21 |
| Example 31 | 38.4 | 24.6 | 15.6 | 18.9 | 2.5 | 4.7 | 65.5 | 34.5 | 0.53 |
| Example 32 | 42.2 |  | 34.2 | 20.8 | 2.7 | 5.7 | 45.0 | 55.0 | 1.22 |
| Example 33 | 35.5 | 45.4 |  | 17.5 | 1.7 | 3.0 | 82.5 | 17.5 | 0.21 |
| Example 34 | 38.7 | 24.7 | 15.7 | 19.0 | 1.9 | 3.6 | 65.3 | 34.7 | 0.53 |
| Example 35 | 42.5 |  | 34.5 | 20.9 | 2.1 | 4.3 | 44.6 | 55.4 | 1.24 |
| Example 36 | 35.7 | 45.6 |  | 17.6 | 1.2 | 2.0 | 82.4 | 17.6 | 0.21 |
| Example 37 | 38.9 | 24.9 | 15.8 | 19.2 | 1.3 | 2.4 | 65.1 | 34.9 | 0.54 |
| Example 38 | 42.8 |  | 34.7 | 21.1 | 1.4 | 2.9 | 44.2 | 55.8 | 1.26 |

TABLE 4

| Sample | Base material POEA Mol % | Base material EA Mol % | Base material ETMA Mol % | Hydrophilic monomer (H) HEMA Mol % | Crosslinkable monomer (C) BDDA Mol % | (H × C) × 10⁻³ | Acrylate Monomer (A) Mol % | Methacrylate Monomer (MA) Mol % | MA/A |
|---|---|---|---|---|---|---|---|---|---|
| Example 39 | 36.7 | 23.5 | 14.9 | 22.6 | 2.4 | 5.4 | 62.6 | 37.4 | 0.60 |
| Example 40 | 40.2 |  | 32.5 | 24.7 | 2.6 | 6.4 | 42.8 | 57.2 | 1.34 |
| Example 41 | 33.0 |  | 40.1 | 24.4 | 2.6 | 6.2 | 35.6 | 64.4 | 1.81 |
| Example 42 | 26.0 |  | 47.4 | 24.0 | 2.5 | 6.1 | 28.5 | 71.5 | 2.50 |
| Example 43 | 19.2 |  | 54.6 | 23.7 | 2.5 | 5.9 | 21.7 | 78.3 | 3.60 |
| Example 44 | 12.7 |  | 61.5 | 23.4 | 2.5 | 5.7 | 15.1 | 84.9 | 5.62 |
| Example 45 | 36.9 | 23.6 | 15.0 | 22.7 | 1.8 | 4.1 | 62.3 | 37.7 | 0.60 |
| Example 46 | 40.4 |  | 32.7 | 24.9 | 2.0 | 4.9 | 42.4 | 57.6 | 1.36 |
| Example 47 | 37.1 | 23.8 | 15.0 | 22.9 | 1.2 | 2.7 | 62.1 | 37.9 | 0.61 |
| Example 48 | 40.7 |  | 33.0 | 25.0 | 1.3 | 3.3 | 42.0 | 58.0 | 1.38 |
| Example 49 | 36.5 |  | 29.6 | 31.5 | 2.4 | 7.4 | 38.9 | 61.1 | 1.57 |
| Example 50 | 30.1 |  | 36.5 | 31.1 | 2.3 | 7.2 | 32.4 | 67.6 | 2.09 |
| Example 51 | 23.7 |  | 43.3 | 30.7 | 2.3 | 7.1 | 26.0 | 74.0 | 2.84 |
| Example 52 | 35.0 |  | 28.3 | 34.4 | 2.3 | 7.8 | 37.2 | 62.8 | 1.69 |
| Example 53 | 33.5 |  | 27.2 | 37.1 | 2.2 | 8.1 | 35.7 | 64.3 | 1.80 |
| Example 54 | 26.2 | 33.5 |  | 38.6 | 1.7 | 6.5 | 61.4 | 38.6 | 0.63 |
| Example 55 | 37.0 | 35.5 | 7.5 | 18.2 | 1.8 | 3.3 | 74.3 | 25.7 | 0.35 |
| Example 56 | 34.0 | 43.5 |  | 20.9 | 1.6 | 3.4 | 79.1 | 20.9 | 0.26 |
| Example 57 | 35.4 | 34.0 | 7.2 | 21.8 | 1.7 | 3.7 | 71.1 | 28.9 | 0.41 |
| Example 58 | 34.2 | 43.7 |  | 21.0 | 1.1 | 2.3 | 79.0 | 21.0 | 0.27 |
| Example 59 | 35.6 | 34.2 | 7.2 | 21.9 | 1.2 | 2.5 | 70.9 | 29.1 | 0.41 |
| Example 60 | 38.8 | 12.4 | 23.6 | 23.9 | 1.3 | 3.0 | 52.5 | 47.5 | 0.90 |

<Physical Property Measurements>
(POEtOH Elution Rate)

Plate-shaped samples were prepared as described above and dried at 60° C. Ten plates having a diameter of 6 mm and a thickness of 0.5 mm were used as samples.

The mass $W_0$ of each plate before treatment was measured. The sample was then immersed in 50 mL of distilled water in a 100 mL pressure-resistant bottle. The pressure-resistant bottle was stored in a dryer at 100° C. throughout testing. The tare weight $W_{01}$ of the bottle, the bottle mass $W_{02}$ after addition of the distilled water, and the bottle mass $W_{03}$ after immersion of the sample were recorded.

The concentrations and elution rates of phenoxyethyl alcohol (POEtOH, hydrolyzate of POEA) were determined for the extract after 30 days of hydrolysis by the following procedure.

After recording the bottle mass $W_{11}$ before extracting the extract solution, the extract solution was collected from the bottle, and the bottle mass $W_{12}$ after collecting the extract solution was recorded. The collected extracts, standard solutions, and blanks (distilled water) thereof were analyzed using HPLC. After analysis, the chromatogram of distilled water was subtracted from the chromatogram of the collected extract solution and standard solution, and baseline correction was performed. The peak area of POEtOH was calculated from the corrected chromatogram. A calibration curve was prepared from the POEtOH concentration of the standard solution and the peak area. Based on the peak area of POEtOH in the extract and the calibration curve obtained, the concentration of POEtOH in the extract was calculated. Using the concentration of POEtOH obtained, the elution rate of POEtOH per 1 g of sample was calculated from the following Equation (1).

$$\text{POEtOH elution rate (\%)} = \text{POEtOH concentration (ppm) in the extraction solution} \times 10^{-6} \times \text{volume of extract solution } V_{1S} \text{ (mL)/mass before treatment } W_0 \text{ (g)} \times 100 \quad \text{Equation (1)}$$

The volume of the extract solution was calculated from the following Equation (2).

$$\text{Volume of extract solution } V_{1S} \text{ (mL} \approx \text{g)} = [W_{02} \text{ (g)} - W_{01}(g)] - [W_{03} \text{ (g)} - W_{11} \text{ (g)}] \quad \text{Equation (2)}$$

In calculating the volume of the extract liquid, the mass change of the sample among the mass changed by heating at 100° C. is negligibly small compared to that of the extract solution. Most of the extract solution is water, so the density of the solution is considered to be 1 g/1 mL. After analyzing the extract on the 30th day of treatment, the bottle was returned to the dryer at 100° C. After a total of 60 days of the hydrolysis treatment, the extract was collected again. The bottle mass $W_{21}$ before collecting the extract was recorded in the same manner as at the 30th day of treatment, the concentration of POEtOH in the extract was quantified by HPLC analysis, and the elution rate of POEtOH was calculated from the following Equation (3).

$$\text{POEtOH elution rate (\%)} = \text{POEtOH concentration (ppm) in extract solution} \times 10^{-6} \times \text{volume of extraction solution } V_{2S} \text{ (mL)/mass before treatment } W_0 \text{ (g)} \times 100 \quad \text{Equation (3)}$$

The volume of the extract solution was calculated from the following Equation (4).

$$\text{Volume of extract solution } V_{2S} \text{ (mL} \approx \text{g)} = V_{1S} \text{ (mL} \approx \text{g)} - [W_{11} \text{ (g)} - W_{12} \text{ (g)}] - [W_{12} \text{ (g)} - W_{21} \text{ (g)}] \quad \text{Equation (4)}$$

Similarly, the elution rate of POEtOH after 90 total days of hydrolysis treatment was also calculated.

(Glistening)

In this measurement, a lens-shaped specimen having a diameter of 6 mm and a center thickness of 0.8 mm+0.1 mm, and a plate-shaped specimen having a diameter of 6 mm and a thickness of 0.5 mm was used. For the lens-shaped sample, the sample was immersed in water at 35° C. for 17 hours or more, then immersed in water at 25° C. for 2 hours, and its appearance was observed with a stereoscopic microscope. For the plate-shaped sample, the sample was immersed in water at 35° C. for 22 hours and then immersed in water at 25° C. for 2 hours, and its appearance was observed with a stereoscopic microscope. The appearance of 2 or 3 samples per sample (Experimental Example) was observed, and the number of occurrences of glistening (bright spots) was examined. The magnification was about 10 to 60 times. For easy observation of glistening, the magnification was suitably adjusted within the above range and observed.

(Tackiness)

In this measurement, a plate having a diameter of 8 mm and a thickness of 0.8 mm was used. A jig for measuring adhesiveness was attached to the sample base (foundation) part of the creep meter. A part of the jig was removed, and the sample was fitted to a part of the removed jig. The integrated jig and sample were attached to the creep meter. The specimen stand was moved, the specimen was brought into contact with the metal probe (radius of curvature: 2.5 mm), a force of 0.05 N was applied, and the table was stopped at that position. About 5 seconds after stopping, the sample and the probe were pulled apart at a separation speed of 1 mm/sec, and the load applied to the probe at that time was measured with a creep meter (RE2—33005S made by Yamaden). From the measured maximum load, the value obtained by subtracting the load (load after detachment) after the probe has separated from the sample was calculated as the value of tackiness. A rating of "A" reflects that the value of tackiness was 0 N or more and less than 0.16 N; a rating of "B" reflects a value of 0.16 N or more and less than 0.30 N; and a rating of "C" reflects a value of 0.30 N or more.

(Refractive Index)

Using an Abbe refractometer, the refractive index of the sample by Hg-e ray was obtained. Measurement was carried out for a sample (25° C.) in a dry state or a sample (35° C.) in a water-absorbing (hydrated) state. As a sample, a plate having a diameter of 6 mm and a thickness of 0.8 mm was used.

(Compression Load)

Figure 5:
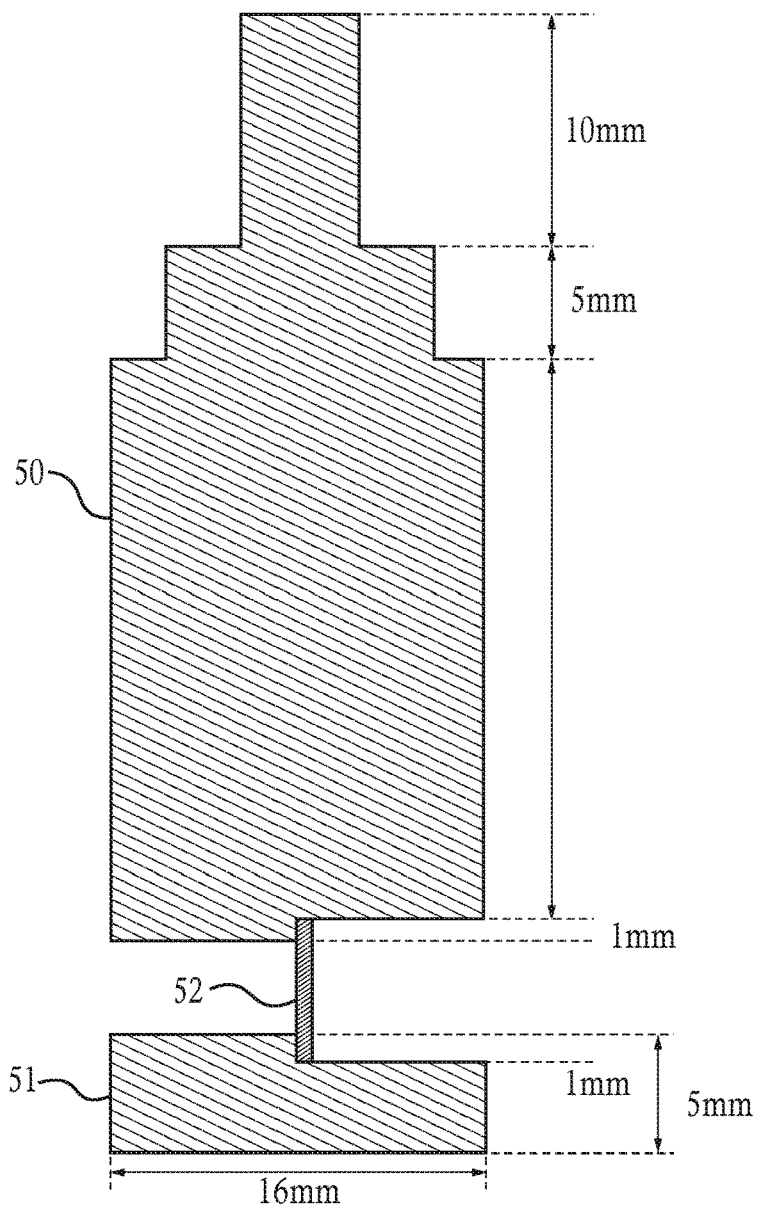
FIG. 5 is a side view of an indenter and a jig used for measuring compressive load.

A plate with a diameter of 6 mm and a thickness of 0.5 mm was compressed and buckled (bending buckled) according to the following procedure, and the load value when the sample was folded from 6 mm to 3 mm was measured as a compressive load value. The state of the sample before measurement was left under an environment of 23° C. and 50% RH, and the condition was adjusted. FIG. 5 is a side view of the indenter 50 and the jig 51 used for measuring the compressive load. The indenter 50 and the jig 51 are formed of polyoxymethylene (duracon) and have a cylindrical shape. The indenter 50 and the jig 51 were attached to a creep meter (RE2—33005S made by Yamaden). Double-sided tape (3M Scotch Brand Tape core series 2-0300) was attached to the sample installation portion on the upper surface of the jig 51, and the sample 52 was set. The sample table (base) portion to which the jig 51 was attached was raised and lowered, and the indenter 50 and the sample 52 were brought into contact with each other. The jig 51 was lifted from the contact position at a compression rate of 0.5 mm/sec to buckle the specimen. The load when raised by 3 mm was taken as the compression load value.

(Elongation Percentage and Breaking Stress)

Figure 6:
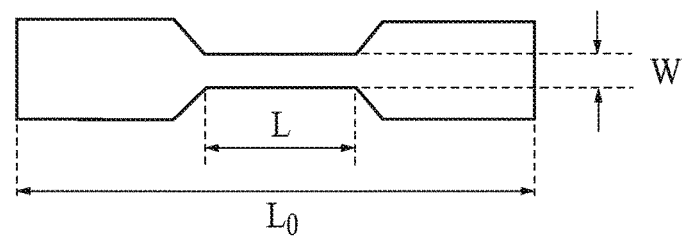
FIG. 6 is an explanatory view of a test piece used for measuring elongation percentage.

The elongation percentage and breaking stress were measured by performing a tensile test using a dumbbell shaped test piece (see FIG. 6) of the polymerized lens material having a total length ($L_0$) of about 20 mm, a parallel part length (L) of 6 mm, a parallel part width (W) of 1.5 mm, and a thickness of 0.8 mm. The test piece was punched out of a plate-shaped polymeric material having a thickness of 0.8 mm using a metal mold. The test piece was immersed in constant-temperature water at 25° C. and allowed to stand for 1 minute, then pulled at a speed of 100 mm/min until breaking. Distortion (=elongation percentage (%)) and breaking stress at maximum load were determined using software.

(Water Absorption Rate)

The mass of the sample in an equilibrium hydrated state and a dry state at 25° C. was measured, and the water absorption rate (mass %) was calculated. The water absorption rate was calculated from the following Equation (5) based on the mass $W_w$ of the sample in equilibrium water-containing state at 25° C. and the mass $W_d$ of the sample in a dry state. Five plates with a diameter of 6 mm and a thickness of 0.8 mm were used as samples.

$$\text{Water absorption rate (mass \%)} = (W_w - W_d)/W_d \times 100 \quad \text{Equation (5)}$$

(Results and Discussion)

The results of Experimental Examples 1 to 14 (lens-shaped samples) are shown in Table 5, and the results of Experimental Examples 15 to 60 (plate-shaped samples) are shown in Tables 6 to 9.

TABLE 5

| Sample | Glistening |
|---|---|
| Example 1 | — |
| Example 2 | — |
| Example 3 | 19 |
| Example 4 | 35 |
| Example 5 | — |
| Example 6 | ∞ |
| Example 7 | 4 |
| Example 8 | — |

TABLE 5-continued

| Sample | Glistening |
|---|---|
| Example 9 | 7 |
| Example 10 | 6 |
| Example 11 | 12 |
| Example 12 | 8 |
| Example 13 | 10 |
| Example 14 | 4 |

[1] Measurement result with lens. Average value of test number n = 2 or 3

TABLE 6

| Sample | POEtOH Elution 100° C. 30 days ppm | Elution rate % | POEtOH Elution 100° C. 60 days ppm | Elution rate % | POEtOH Elution 100° C. 90 days ppm | Elution rate % | Glistening Count[1] | Tackiness —[2] | Refractive Index 25° C. Dry | Refractive Index 35° C. Wet | Breaking stress MPa | Elongation percentage % | Water absorption rate % |
|---|---|---|---|---|---|---|---|---|---|---|---|---|---|
| Example 15 | 1 | 0.04 | 4 | 0.11 | 3 | 0.10 | — | — | — | — | — | — | — |
| Example 16 | 2 | 0.05 | 4 | 0.13 | 5 | 0.15 | 10 | — | — | — | — | — | — |
| Example 17 | — | — | — | — | — | — | — | — | — | — | — | 139 | — |
| Example 18 | 3 | 0.08 | 8 | 0.23 | 15 | 0.39 | 2 | — | — | — | — | — | — |
| Example 19 | 6 | 0.18 | 40 | 1.24 | 192 | 5.57 | 2 | B | 1.523 | 1.517 | 3.9 | — | 1.7 |
| Example 20 | 3 | 0.10 | 15 | 0.43 | 49 | 1.31 | — | — | 1.525 | 1.519 | 5.6 | — | 1.8 |
| Example 21 | 2 | 0.06 | 7 | 0.21 | 15 | 0.41 | 0 | A | 1.527 | 1.522 | — | — | 1.9 |

[1] The result is for a plate with a diameter of 6 mm and a thickness of 0.5 mm, and the average value of the number of tests n = 3.
[2] A: 0N or more and less than 0.16N, B: 0.16N or more and less than 0.30N, C: 0.30N or more

TABLE 7

| Sample | POEtOH Elution 100° C. 30 days ppm | Elution rate % | POEtOH Elution 100° C. 60 days ppm | Elution rate % | POEtOH Elution 100° C. 90 days ppm | Elution rate % | Glistening Count[1] | Tackiness —[2] | Refractive Index 25° C. Dry | Refractive Index 35° C. Wet | Breaking stress MPa | Elongation percentage % | Water absorption rate % |
|---|---|---|---|---|---|---|---|---|---|---|---|---|---|
| Example 22 | 6 | 0.19 | 43 | 1.28 | 205 | 5.80 | — | C | 1.523 | 1.517 | 3.4 | — | 1.6 |
| Example 23 | 3 | 0.11 | 15 | 0.48 | 53 | 1.56 | — | — | 1.525 | 1.519 | — | — | 1.8 |
| Example 24 | 2 | 0.06 | 5 | 0.16 | 10 | 0.27 | — | A | 1.527 | 1.521 | 11.7 | — | 2.0 |
| Example 25 | 6 | 0.18 | 43 | 1.16 | 209 | 5.29 | — | C | 1.523 | 1.518 | — | — | 1.6 |
| Example 26 | 5 | 0.13 | 25 | 0.67 | 111 | 2.76 | — | — | — | — | — | — | — |
| Example 27 | 3 | 0.09 | 16 | 0.40 | 51 | 1.24 | — | — | 1.525 | 1.519 | — | — | 1.8 |
| Example 28 | 3 | 0.09 | 12 | 0.32 | 33 | 0.86 | — | — | — | — | — | — | — |
| Example 29 | 2 | 0.05 | 6 | 0.16 | 11 | 0.28 | — | — | 1.527 | 1.521 | — | 345 | 2.1 |
| Example 30 | 5 | 0.16 | 36 | 1.06 | 162 | 4.48 | — | B | 1.522 | 1.516 | — | — | 2.1 |
| Example 31 | 3 | 0.10 | 15 | 0.41 | 44 | 1.17 | — | B | 1.524 | 1.518 | — | — | 2.4 |
| Example 32 | 2 | 0.06 | 6 | 0.17 | 10 | 0.28 | — | A | 1.527 | 1.521 | 11.8 | — | 2.4 |
| Example 33 | 5 | 0.15 | 33 | 0.97 | 150 | 4.09 | — | B | 1.522 | 1.516 | — | — | 2.3 |
| Example 34 | 3 | 0.09 | 12 | 0.37 | 38 | 1.06 | 0 | B | 1.524 | 1.518 | 6.1 | — | 2.2 |
| Example 35 | 2 | 0.06 | 6 | 0.18 | 10 | 0.29 | — | A | 1.527 | 1.520 | 11.3 | — | 2.7 |
| Example 36 | 6 | 0.17 | 38 | 1.03 | 176 | 4.47 | — | C | 1.522 | 1.516 | 4.4 | — | 2.2 |
| Example 37 | 3 | 0.08 | 13 | 0.33 | 41 | 0.97 | 1 | B | 1.524 | 1.518 | 6.5 | — | 2.5 |
| Example 38 | 2 | 0.06 | 6 | 0.17 | 12 | 0.30 | — | A | 1.527 | 1.520 | — | — | 2.8 |

[1] The result is for a plate with a diameter of 6 mm and a thickness of 0.5 mm, and the average value of the number of tests n = 3.
[2] A: 0N or more and less than 0.16N, B: 0.16N or more and less than 0.30N, C: 0.30N or more

TABLE 8

| Sample | POEtOH Elution 100° C. 30 days ppm | Elution rate % | POEtOH Elution 100° C. 60 days ppm | Elution rate % | POEtOH Elution 100° C. 90 days ppm | Elution rate % | Glistening Count[1] | Tackiness —[2] | Refractive Index 25° C. Dry | Refractive Index 35° C. Wet | Breaking stress MPa | Compression load —[3] | Water absorption rate % |
|---|---|---|---|---|---|---|---|---|---|---|---|---|---|
| Example 39 | 3 | 0.09 | 13 | 0.36 | 37 | 0.95 | — | A | 1.524 | 1.517 | 8.3 | — | — |
| Example 40 | 2 | 0.06 | 6 | 0.18 | 10 | 0.27 | — | A | 1.526 | 1.520 | 15.6 | — | — |
| Example 41 | 2 | 0.06 | 5 | 0.16 | 10 | 0.27 | — | — | 1.520 | 1.512 | — | — | — |

TABLE 8-continued

| Sample | POEtOH Elution 100° C. 30 days | | POEtOH Elution 100° C. 60 days | | POEtOH Elution 100° C. 90 days | | Glistening Count[1] | Tackiness [2] | Refractive Index | | Breaking stress MPa | Compression load [3] | Water absorption rate % |
|---|---|---|---|---|---|---|---|---|---|---|---|---|---|
| | ppm | Elution rate % | ppm | Elution rate % | ppm | Elution rate % | | | 25° C. Dry | 35° C. Wet | | | |
| Example 42 | 2 | 0.05 | 4 | 0.13 | 7 | 0.20 | — | — | 1.514 | 1.507 | — | — | — |
| Example 43 | 2 | 0.06 | 5 | 0.13 | 7 | 0.18 | — | — | 1.509 | 1.500 | — | 0.7 | — |
| Example 44 | 1 | 0.04 | 3 | 0.09 | 4 | 0.12 | — | — | 1.503 | 1.495 | — | — | — |
| Example 45 | 2 | 0.07 | 10 | 0.29 | 29 | 0.79 | 1 | A | 1.524 | 1.517 | 9.3 | — | — |
| Example 46 | 2 | 0.05 | 5 | 0.16 | 8 | 0.23 | — | A | 1.526 | 1.520 | 17.7 | — | — |
| Example 47 | 3 | 0.09 | 13 | 0.34 | 36 | 0.88 | — | B | 1.524 | 1.517 | 9.7 | — | — |
| Example 48 | 2 | 0.06 | 6 | 0.17 | 11 | 0.29 | — | A | 1.526 | 1.519 | 16.7 | — | — |
| Example 49 | 2 | 0.06 | 6 | 0.19 | 13 | 0.36 | — | — | — | — | — | 0.8 | — |
| Example 50 | 2 | 0.06 | 5 | 0.15 | 9 | 0.25 | — | — | 1.520 | 1.510 | — | 1.1 | — |
| Example 51 | 2 | 0.05 | 4 | 0.12 | 7 | 0.18 | — | — | 1.514 | 1.504 | — | 1.3 | — |
| Example 52 | 2 | 0.07 | 7 | 0.19 | 15 | 0.36 | — | — | — | — | — | 1.8 | — |
| Example 53 | 2 | 0.06 | 6 | 0.18 | 11 | 0.32 | — | — | — | — | — | 1.6 | — |
| Example 54 | 4 | 0.14 | 20 | 0.60 | 63 | 1.77 | — | — | — | — | — | 1.0 | — |

[1]The result is for a plate with a diameter of 6 mm and a thickness of 0.5 mm, and the average value of the number of tests n = 3.
[2]A: 0N or more and less than 0.16N, B: 0.16N or more and less than 0.30N, C: 0.30N or more
[3]The compression load of Example 54 was set to "1", and the values of each experimental example were standardized.

TABLE 9

| Sample | POEtOH Elution 100° C. 30 days | | POEtOH Elution 100° C. 60 days | | POEtOH Elution 100° C. 90 days | |
|---|---|---|---|---|---|---|
| | ppm | Elution rate % | ppm | Elution rate % | ppm | Elution rate % |
| Example 55 | 5 | 0.14 | 24 | 0.66 | 91 | 2.33 |
| Example 56 | 5 | 0.15 | 31 | 0.83 | 134 | 3.33 |
| Example 57 | 5 | 0.13 | 23 | 0.61 | 79 | 1.92 |
| Example 58 | 4 | 0.14 | 28 | 0.82 | 119 | 3.31 |
| Example 59 | 5 | 0.13 | 23 | 0.60 | 79 | 1.96 |
| Example 60 | 3 | 0.09 | 11 | 0.30 | 25 | 0.63 |

From the results of Tables 6 to 9, it was found that hydrolysis can be suppressed by increasing the content of the methacrylate structure in the lens material, and that alkoxy methacrylate is suitable as such a methacrylate component. In Experimental Examples to which MTMA or ETMA (alkoxy methacrylates) was added, elution of POEtOH was comparatively small, hydrolysis was suppressed, and the material was not high in tackiness.

The breaking stress was evaluated for each of Experimental Examples 19, 20, 22, 24, 32, 34-37, 39, 40, and 45-48. Samples having a ratio MA/A within the range of 0.25 to 1.25, and especially 0.30 to 0.70, exhibited a favorable balance of breaking stress and reduced glistening, as shown in FIG. 4. In particular, Experimental Examples 20, 24, 32, 34, 35, 37, 39, 45, and 47 had ratios MA/A ranging from 0.45 to 1.24, and had a breaking stress within the range of 5.6 to 11.8. The materials had sufficient elasticity (permitting easy folding) and yet could withstand a large degree of stress before failing. Only one occurrence of glistening was observed for any of the samples evaluated. However, Experimental Examples 19, 22, 36, 40, 46, and 48 had ratios MA/A outside the disclosed range. Experimental Examples 19, 22, and 36 had low breaking stress values, while Experimental Examples 40, 46, and 48 were difficult to fold.

From the results of Tables 5 to 9, it was found that the addition amount of alkoxyalkyl methacrylate is preferably 5 mol % to 55 mol %, preferably 6 mol % to 30 mol %, and more preferably 7 mol % to 20 mol %. The minimum amount of alkoxyalkyl methacrylate is preferably in the above range from the viewpoint of suppression of hydrolysis, and the maximum amount of alkoxyalkyl methacrylate is preferably within the above-mentioned range from the viewpoint of facilitating folding.

From the viewpoint of providing a lens with a refractive index in the hydrated state of 1.50 or more, the content of the aromatic ring-containing acrylate is preferably 19 mol % to 46 mol %, preferably 34 mol % to 43 mol %, and more preferably 35 mol % to 39 mol %. The higher the refractive index of the material, the thinner the lens can be, making it easier to insert the lens into the eye in the folded state.

From the viewpoint of suppressing the occurrence of glistening, the content of the hydrophilic monomer is preferably 10 mol % to 40 mol %, preferably 13 mol % to 25 mol %, and more preferably 15 mol % to 24 mol % in order to facilitate folding of the lens in the dry state. A lens that can be easily bent in the dry state can be more easily stored, handled, and mounted into the insertion instrument.

Experimental Example 54 shown in Table 8 is a material described in JP-A-11-56998, which can be folded but requires considerably extra force to do so. This material is used as a reference, and the value is set to 1. If the compressive load value of a sample is greater than or equal to the value of this material, it is judged to be difficult to fold.

In Experimental Examples 50 to 53 shown in Table 8, the elution of POEtOH was reduced by containing ETMA, and the effect of suppressing hydrolysis was obtained, but the content of ETMA or HEMA was large and foldability was poor.

From the viewpoint of suppressing the occurrence of glistening and improving shape recoverability after intraocular insertion, the content of the crosslinkable monomer is 2 parts by mass or more and 4 parts by mass or less with respect to 100 parts by mass of the base material.

Although only a few example embodiments have been described in detail above, those skilled in the art will readily appreciate that many modifications are possible in the example embodiments without materially departing from the disclosed embodiments. Accordingly, all such modifications are intended to be included within the scope of this disclosure as defined in the following claims.

What is claimed is:

1. An intraocular lens comprising a polymeric lens material that is formed from a polymerizable composition comprising:
   (a) a single aromatic acrylate monomer which is an aromatic-ring containing acrylate;
   (b) an alkoxyalkyl methacrylate monomer having an alkoxyalkyl group with 4 or less carbon atoms;
   (c) an alkyl acrylate monomer having an alkyl group with 1 to 20 carbon atoms;
   (d) a hydrophilic monomer; and
   (e) a crosslinkable monomer,
   wherein a molar ratio H:C (molar amount H of the hydrophilic monomer:molar amount C of the crosslinkable monomer) in the polymerizable composition is from 12:1 to 15:1.

2. An intraocular lens comprising a polymeric lens material that is formed from a polymerizable composition comprising:
   (a) a single aromatic acrylate monomer which is an aromatic-ring containing acrylate;
   (b) an alkoxyalkyl methacrylate monomer having an alkoxyalkyl group with 4 or less carbon atoms;
   (c) an alkyl acrylate monomer having an alkyl group with 1 to 20 carbon atoms;
   (d) a hydrophilic monomer; and
   (e) a crosslinkable monomer,
   wherein:
   the single aromatic acrylate monomer, the alkoxyalkyl methacrylate monomer, and the alkyl acrylate monomer constitute a base material of the polymerizable composition, and
   the polymerizable composition comprises, per 100 parts by mass of the base material:
   from 55 parts to 65 parts by mass of the single aromatic acrylate monomer;
   from 10 parts to 25 parts by mass of the alkoxyalkyl methacrylate monomer;
   from 15 parts to 30 parts by mass of h alkyl acrylate monomer;
   from 15 parts to 30 parts by mass of the hydrophilic monomer; and
   from 2 parts to 4 parts by mass of the crosslinkable monomer.

3. The intraocular lens according to claim 2, wherein:
   the single aromatic acrylate monomer is phenoxyethyl acrylate,
   the alkoxyalkyl methacrylate monomer is ethoxyethyl methacrylate,
   the alkyl acrylate monomer is ethyl acrylate.

4. The intraocular lens according to claim 3, wherein the hydrophilic monomer is 2-hydroxyethyl methacrylate.

5. An intraocular lens comprising a polymeric lens material that is formed from a polymerizable composition comprising:
   (a) 35 mol % to 39 mol % of a single aromatic acrylate monomer which is an aromatic-ring containing acrylate;
   (b) 7 mol % to 20 mol % of an alkoxyalkyl methacrylate monomer having an alkoxyalkyl group with 4 or less carbon atoms;
   (c) 20 mol % to 37 mol % of an alkyl acrylate monomer having an alkyl group with 1 to 20 carbon atoms;
   (d) 15 mol % to 24 mol % of a hydrophilic monomer; and
   (e) 1.1 mol % to 2.1 mol % of a crosslinkable monomer.

6. The intraocular lens according to claim 5, wherein:
   the single aromatic acrylate monomer is phenoxyethyl acrylate,
   the alkoxyalkyl methacrylate monomer is ethoxyethyl methacrylate,
   the alkyl acrylate monomer is ethyl acrylate.

7. The intraocular lens according to claim 6, wherein the hydrophilic monomer is 2-hydroxyethyl methacrylate.

8. The intraocular lens according to claim 1, wherein a molar amount of the crosslinkable monomer in the polymerizable composition is less than 2.1 mol %.

9. The intraocular lens according to claim 1, wherein an H×C value of the lens material is more than $3.6 \times 10^{-3}$ and less than $4.2 \times 10^{-3}$, the H×C value being the product of a molar amount H of the hydrophilic monomer and a molar amount C of the crosslinkable monomer in the polymerizable composition.

10. The intraocular lens according to claim 1, wherein a molar ratio MA/A of all methacrylate monomers to all acrylate monomers in the polymerizable composition is in the range of 0.35 to 0.65.

11. The intraocular lens according to claim 1, wherein the polymeric lens material has an elution characteristic of 1.30 mass % or less at 90 days.

12. The intraocular lens according to claim 1, wherein the lens material has a breaking stress of from 5.5 MPa to 11.0 MPa.

13. The intraocular lens according to claim 1, wherein the lens material has a refractive index of 1.50 or more in a state of hydration.

14. The intraocular lens according to claim 1, the lens being formed by molding.

* * * * *